United States Patent [19]

Bellut

[11] Patent Number: 4,845,303

[45] Date of Patent: Jul. 4, 1989

[54] PROCEDURE FOR THE PRODUCTION OF BETA-ISOPHORONE FROM ALPHA-ISOPHORONE

[75] Inventor: Hans Bellut, Duelmen, Fed. Rep. of Germany

[73] Assignee: Huels Aktiengesellschaft, Marl, Fed. Rep. of Germany

[21] Appl. No.: 235,477

[22] Filed: Aug. 24, 1988

[30] Foreign Application Priority Data

Oct. 17, 1987 [DE] Fed. Rep. of Germany ....... 3735211

[51] Int. Cl.$^4$ ............................................. C07C 45/67
[52] U.S. Cl. .................................................... 568/341
[58] Field of Search ........................................ 568/341

[56] References Cited

U.S. PATENT DOCUMENTS

| | | | |
|---|---|---|---|
| 2,917,539 | 12/1959 | Isler et al. | 568/347 |
| 2,918,495 | 12/1959 | Booth | 568/341 |
| 4,005,145 | 1/1977 | Wider | 568/341 |
| 4,010,205 | 3/1977 | Becker et al. | 568/344 |

FOREIGN PATENT DOCUMENTS 52-39655  3/1977  Japan ................................. 568/341

*Primary Examiner*—James H. Reamer
*Attorney, Agent, or Firm*—Oblon, Spivak, McClelland, Maier & Neustadt

[57] ABSTRACT

A process for the production of beta-isophorone from alpha-isophorone, comprising the steps of:
(i) heating alpha-isophorone in the presence of an isomerization catalyst, said catalyst comprising a metal acetylacetonate, wherein said metal is selected from the group consisting of aluminum and the metals of Groups IVB, VB, VIB, VIIB and VIIIB of the periodic table, to produce beta-isophorone, and
(ii) isolating said beta-isophorone.

6 Claims, No Drawings

PROCEDURE FOR THE PRODUCTION OF BETA-ISOPHORONE FROM ALPHA-ISOPHORONE

BACKGROUND OF THE INVENTION

1. Field of the Invention

The present invention relates to the catalytic isomerization of alpha-isophorone to beta-isophorone.

2. Discussion of the Background

Beta-isophorone is of great economic interest as a basic organic material for organic preparations, for example, in the perfume industry as well as a starting product for various vitamin syntheses. However, in the well-known trimerization of acetone the product is mainly alpha-isophorone in more than 90% yield. A high yield, simple conversion of the alpha-isomer to the beta-isomer is of particular interest, as it is possible to synthesize from the beta-isomer, natural products, which produce little or no problems in their effect or their degradation behavior.

The shifting of the double bond in the isophorone molecule resulting from the synthesis of alpha-isophorone produces great problems because (1) the double bond must be shifted out of conjugation with the carbonyl group, (2) the system easily reacts to stronger alkali or even acid catalysts with dehydration of the compounds and polymerization, (3) the energy content of the molecule must be clearly raised and (4) the adjustment of the equilibrium takes place only slowly.

Due to the relatively small amount of beta-isophorone existing at equilibrium, the continuous removal of the desired isomer causes considerable technical problems; however, it is not in each case a prerequisite for a practical procedure. As no changes can be made in the equilibrium for generally known thermodynamic reasons, it was possible only to attempt to influence the rate of the equilibrium adjustment without causing an increase in side reactions.

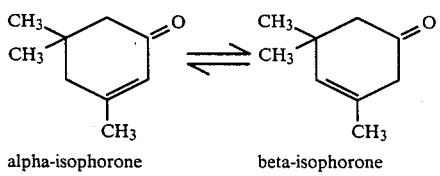

alpha-isophorone        beta-isophorone

A number of methods for the preparation of beta-isophorone are known. However, all of these methods have considerable disadvantages, so that to date none of these methods can be converted into practice or utilized on a technically applicable scale. A molecular rearrangement can be produced, e.g., by the conversion of molar quantities of alpha-isophorone with methylmagnesiumiodide with the addition of iron(III)chloride, subsequent hydrolysis and distillative processing (A. Heymes and P. Teisseire, Recherches 1971, 18, 104–8). The isomerization also takes place upon several hours of boiling with triethanolamine, subsequent fractionation and washing of the distillate with tartaric acid and salt solution (Firmenich S. A., DE-OS No. 24 57 157). The conversion is also possible by catalysis with weakly dissociated organic acids. In one such procedure the yield is about 70% of pure beta-isophorone with the use of adipic acid (Hoffmann-La Roche & Co. AG, DE-PS No. 25 08 779).

All the known procedures have the disadvantage that either the use of large volumes of chemicals are required with the related reprocessing and waste disposal problems or that the catalysts used are too weakly alkaline or acidic to realize an acceptable space/time yield. A simple increase or reduction of the acidity of the catalyst is not possible as otherwise there is increased polymerization and dehydration by self-condensation of the isophorone.

SUMMARY OF THE INVENTION

Accordingly, one object of the present invention is a procedure for obtaining beta-isophorone from alpha-isophorone which does not have the disadvantages of the known processes, is less expensive and leads to high yields of beta-isophorone.

This and other objects which will become apparent from the following specification have been achieved by the present process for the production of beta-isophorone from alpha-isophorone which comprises (i) heating alpha-isophorone in the presence of an isomerization catalyst, said catalyst comprising a metal acetylacetonate, wherein said metal is selected from the group consisting of aluminum and the metals of Groups IVB, VB, VIB, VIIB and VIIIB of the periodic table, to produce beta-isophorone, and (ii) isolating said beta-isophorone.

DETAILED DESCRIPTION OF THE PREFERRED EMBODIMENTS

The present invention is a procedure for the production of beta-isophorone from alpha-isophorone, wherein alpha-isophorone is eated, preferably with distillation in the presence of acetylacetonates of aluminum and the metals of groups IVB, VB, VIB, VIIB and VIIIB of the periodic table.

The group assignment is done according to the designation in Chemical Abstracts. Particularly suitable catalysts are the acetylacetonates of Fe, Co, Cr, Mn and Al.

By complex formation, the strength of the Friedel-Crafts compounds, such as $AlCl_3$, $FeCl_3$ etc. is greatly reduced. However, the isomerization capability for double bonds in delicate system is at least in part maintained.

It has been shown in tests that, in general, transition metal acetylacetonates are particularly suited as carbon-carbon double bond shifting catalysts. Although the metal atoms are very tightly bound in these complexes, they can greatly increase the rate of adjustment of the equilibrium. For the present isomerization, only 0.01 to 10% by weight, preferably 0.1 to 1.0% by weight of the metal acetylacetonates are needed. The considerable reduction in catalyst quantity relative to known methods must be regarded as an important process improvement. In addition, the reaction time is reduced by at least 50%, which leads to a doubling of the space/time yield with comparable design of the apparatus.

The procedure of the present process is technically relatively simple and can be executed continuously or discontinuously, i.e., batchwise.

It is preferable to perform the isomerization in conjunction with a distillation process to remove the beta-isophorone as it is formed. However any other means of separating the beta-isomer from the isomerized reaction product is considered to be within the scope of the present invention.

In a preferred embodiment, fresh technical grade isophorone is continuously metered into a distillation apparatus containing alpha-isophorone and 0.1 to 1% by weight of a transition metal acetylacetonate. The addition of alpha-isophorone is made in an amount such that an overhead fraction containing beta-isophorone can be withdrawn from the fractioning column. The beta-isophorone obtained in this manner has a purity of about 95% and can be further concentrated as desired by additional fractional distillation. The heat energy required for isomerization is provided by the boiling distillation residue in the apparatus working at normal pressure. With this procedure, a heat temperature of 187° C. is easily attained. In spite of the significant progress made, the present procedure does not work completely without loss; about 5 to 7% of the isophorone collected by condensation of the overhead fraction must be rejected. However, a yield of 90 to 95% of beta-isophorone, relative to the starting material, may be expected.

It is preferable to operate at normal atmospheric pressure, in order to use the boiling point difference between alpha and beta-isomers of isophorone. When working at reduced pressure, the boiling point difference is reduced and the demands on the separation capabilities of the distillation column are increased.

Other features of the invention will become apparent in the course of the following description of exemplary embodiments which are given for illustration of the invention and are not intended to be limiting thereof.

EXAMPLES

Example 1

From a 1 L flask, 500 ml technical isophorone (GC analysis: 98.7% alpha-isophorone, 0.98% beta-isophorone) are distilled off through a fractioning column after mixing with 2 g of iron(III)acetylacetonate (corresponding to 0.43% by weight). A 1 m column with 2.5 cm diameter and "Multifil" V4A packing material, with a preheater set at 155° C. is sufficient to obtain adequate isomerization. The required distillation vessel temperature is 215° C. at the beginning, but must be raised to 250° C. towards the end of the distillation. As soon as the apparatus is at equilibrium, a temperature of 186° C. is maintained as the distillation head temperature. The system remains stable at a reduction/reflux ratio of 1:10. With the described column size it is possible to obtain 20 ml of the product per hour.

The isolated product weighed 445 g, corresponding to 89% raw yield (CG analysis: 94% beta-isophorone, 5% alpha-isophorone), with 55 g (11% by weight) residue remaining in distillation vessel. The residue consists (see example 4) of 70 to 80% alpha-isophorone and can be recycled to the apparatus after purification.

Simple distillation of the product through a 40 cm Vigreux column with a reduction of 100 ml/h resulted in 99% beta-isophorone as the raw product. If the recycled alpha-isophorone is taken into account, a pure yield of 97 to 98% beta-isophorone is obtained with this procedure.

Examples 2 to 9

In the same manner as in Example 1, isomerization is conducted with different catalysts. The results are shown in the following table:

TABLE

| Example No. | Catalyst metal | Catalyst (%) | Product yield (ml/h) | Yield raw (%) | Yield pure (% conv.) | Residue (%) |
|---|---|---|---|---|---|---|
| 2 | Fe(III) | 0.44 | 20 | 80 | 95.4 | 20[a] |
| 3 | Co(III) | 1.0 | 20 | 77 | 93.9 | 22[a] |
| 4 | Co(III) | 1.0 | 20 | 77 | 94.7 | 23[a] |
| 5 | Cr(III) | 1.0 | 10 | 74 | 93.3 | 25[a] |
| 6 | Al(III) | 1.0 | 10–15 | 77 | 94.7 | 23[a] |
| 7 | Ni(II)[b] | 1.0 | 10 | 48 | — | — |
| 8 | Mn(II) | 1.0 | 20–10 | 73 | 93.0 | 26[a] |
| 9 | Ti(IV)[b] | 1.0 | 20 | 44 | — | — |

[a]The residue is 77% (GC analysis) alpha-isophorone which can be recycled.
[b]The catalyst lost its activity in the course of the test.

Example 10

Analogous to Example 1, 1800 g alpha-isophorone are isomerized with 0.11% by weight iron(III)acetylacetonate when the distilled raw product is continuously replaced by fresh starting product. A raw yield of 84% is attained with 15% retained as residue.

Obviously, numerous variations and modifications of the invention are possible in light of the above teachings. Therefore, in light of the above teachings, it is to be understood that the invention may be practiced other than as specifically described herein.

What is claimed as new and desired to be secured by Letters Patent of the United States is:

1. A process for the production of beta-isophorone from alpha-isophorone, comprising the steps of:
   (i) heating alpha-isophorone in the presence of an isomerization catalyst, said catalyst comprising a metal acetylacetonate, wherein said metal is selected from the group consisting of aluminum and the metals of Groups IVB, VB, VIB, VIIB and VIIIB of the periodic table, to produce beta-isophorone, and
   (ii) isolating said beta-isophorone.

2. The process of claim 1, wherein said heating and isolating steps are conducted by distilling said alpha-isophorone in the presence of said catalyst.

3. The process of claim 1, wherein said heating is conducted at a temperature from about 215° C. to about 250° C. at atmospheric pressure.

4. The process of claim 1, wherein said metal is Fe, Co, Cr, Mn or Al.

5. The process of claim 1, wherein 0.01–10.0 wt. % of said catalyst is used in said heat step.

6. The process of claim 5, wherein 0.1–1.0 wt. % of said catalyst is used in said heating step.

* * * * *